United States Patent
Park et al.

(10) Patent No.: US 10,980,993 B2
(45) Date of Patent: Apr. 20, 2021

(54) MICRONEEDLE, APPARATUS FOR MANUFACTURING MICRONEEDLE, AND METHOD OF MANUFACTURING MICRONEEDLE USING APPARATUS

(71) Applicant: GACHON UNIVERSITY OF INDUSTRY-ACADEMIC COOPERATION FOUNDATION, Seongnam-si (KR)

(72) Inventors: Jung Hwan Park, Seongnam-si (KR); Hye Rin Jeong, Daegu (KR); Jee Hyun Park, Seoul (KR)

(73) Assignee: GACHON UNIVERSITY OF INDUSTRY-ACADEMIC COOPERATION FOUNDATION, Seongnam-si (KR)

(*) Notice: Subject to any disclaimer, the term of this patent is extended or adjusted under 35 U.S.C. 154(b) by 85 days.

(21) Appl. No.: 16/176,087

(22) Filed: Oct. 31, 2018

(65) Prior Publication Data

US 2020/0129745 A1 Apr. 30, 2020

(51) Int. Cl.
*A61M 37/00* (2006.01)

(52) U.S. Cl.
CPC . *A61M 37/0015* (2013.01); *A61M 2037/0023* (2013.01); *A61M 2037/0053* (2013.01)

(58) Field of Classification Search
CPC ........ B05D 5/00; A61K 43/00; A61K 39/145; A61M 37/0015; A61M 37/0023
See application file for complete search history.

(56) References Cited

U.S. PATENT DOCUMENTS

| | | | |
|---|---|---|---|
| 4,450,150 A * | 5/1984 | Sidman | A61D 7/00 252/62.53 |
| 7,648,484 B2 | 1/2010 | Yeshurun et al. | |
| 2009/0017210 A1* | 1/2009 | Andrianov | A61K 9/0021 427/256 |
| 2009/0241554 A1* | 10/2009 | Nishida | H01L 35/30 62/3.6 |
| 2014/0044851 A1* | 2/2014 | Kennedy | A47J 27/004 426/523 |
| 2018/0185625 A1* | 7/2018 | Baek | B29C 33/424 |

FOREIGN PATENT DOCUMENTS

| | | |
|---|---|---|
| JP | 4750347 B2 | 8/2011 |
| KR | 10-2014-0006167 A | 1/2014 |

* cited by examiner

*Primary Examiner* — Dah-Wei D. Yuan
*Assistant Examiner* — Andrew J Bowman
(74) *Attorney, Agent, or Firm* — Sughrue Mion, PLLC (57) ABSTRACT

Disclosed are a microneedle, an apparatus for manufacturing a microneedle including a support part containing a medicinal solution for coating a microneedle, a controller for controlling the temperature of the medicinal solution contained in the support part, and a dryer for drying the medicinal solution coated on the microneedle, and a method of manufacturing the microneedle using the apparatus. According to the configuration, the temperature of the medicinal solution can be adjusted such that a viscosity suitable for coating with the medicinal solution is maintained, whereby the quality of a microneedle coated with the medicinal solution can be improved, and denaturation of active ingredients in the medicinal solution can be prevented, which causes stability increase.

7 Claims, 6 Drawing Sheets

MICRONEEDLE, APPARATUS FOR MANUFACTURING MICRONEEDLE, AND METHOD OF MANUFACTURING MICRONEEDLE USING APPARATUS

BACKGROUND OF THE DISCLOSURE

Field of the Disclosure

The present disclosure relates to a microneedle, an apparatus for manufacturing the microneedle, and a method of manufacturing the microneedle using the apparatus. More particularly, the present disclosure relates to an apparatus for manufacturing a microneedle capable of adjusting the temperature of a supporter, in which a medicinal coating solution for manufacturing a microneedle is contained, and a manufacturing environment, which includes a step of preparing a medicinal coating solution, a step of coating with the medicinal coating solution, and a step of drying the medicinal coating solution, to control the viscosity of the medicinal coating solution and improve the stability of active ingredients in the medicinal solution, and a method of manufacturing a microneedle using the apparatus.

Description of the Related Art

A transdermal drug delivery system is disadvantageous in that the molecular weight of a drug capable of being delivered is limited. Accordingly, a variety of active transdermal drug delivery systems have been recently proposed. Thereamong, a microneedle of penetrating the stratum corneum to directly administer a drug to the skin layer have attracted great attention. A microneedle, which serves to deliver a drug into the skin by forming fine holes in the outermost skin layer, the stratum corneum, can be manufactured to have various lengths of 90 to 1500 µm depending upon the purpose of drug delivery.

Coated microneedles, which are a type of a microneedle, are manufactured by coating a surface of a microneedle with a composition containing a drug to be delivered. Such coated microneedles are advantageous in that a manufacturing process is simple and economic efficiency is high. Meanwhile, coated microneedles are disadvantageous in that it is difficult to control the viscosity due to a coating process carried out at room temperature and active ingredients can be deformed due to room temperature exposure. Therefore, various research has recently been conducted to easily control the viscosity of a microneedle and thus accomplish improved administration.

RELATED ART DOCUMENTS

Patent Documents (Patent Document 1) Korean Patent Application Publication No. 2014-0006167
(Patent Document 2) Japanese Patent No. 4750347

SUMMARY OF THE DISCLOSURE

Therefore, the present disclosure has been made in view of the above problems, and it is one object of the present disclosure to provide a microneedle uniformly coated with a medicinal solution and exhibiting improved stability of active ingredients included in the medicinal solution, by controlling the viscosity of the medicinal solution through temperature adjustment, an apparatus for manufacturing the microneedle, and a method of manufacturing the microneedle using the apparatus.

In accordance with an aspect of the present disclosure, the above and other objects can be accomplished by the provision of an apparatus for manufacturing a microneedle coated with a medicinal solution, the apparatus including a support part containing a medicinal solution for coating a microneedle; and a controller configured to control the temperature of the medicinal solution contained in the support part, wherein the controller lowers the temperature of the medicinal solution and maintains the temperature at a predetermined temperature.

According to an aspect of the present disclosure, the support part may be a container with an open top, and the controller may be provided at a bottom of the support part and may serve to lower the temperature of the support part to a low temperature.

According to an aspect of the present disclosure, the controller may include a temperature holding member installed at a bottom of the support part and configured to maintain the temperature of the medicinal solution; and a cooling member provided at a bottom of the support part and configured to cool the support part, wherein the temperature holding member is provided between the cooling member and the support part.

According to an aspect of the present disclosure, the temperature holding member may include a Peltier effect device, and the cooling member may include a cooling fan cooled by a refrigerant.

According to an aspect of the present disclosure, the apparatus may further include a chamber, wherein the support part and the controller are installed in the chamber and an internal temperature of the chamber is adjustable.

According to an aspect of the present disclosure, an inside of the chamber may be cooled and is maintained at a predetermined temperature, and a process of immersing the microneedle in the support part to coat a surface of the microneedle with a medicinal solution may be performed inside the chamber cooled to low temperature.

According to an aspect of the present disclosure, the apparatus may further include a dryer configured to dry the microneedle coated with the medicinal solution, wherein the dryer serves to adjust temperature.

According to an aspect of the present disclosure, the dryer may be cooled and may be maintained at a predetermined temperature.

In accordance with another aspect of the present disclosure, there is provided an apparatus for manufacturing a microneedle coated with a medicinal solution, wherein the apparatus includes a support part containing a medicinal solution for coating a microneedle; a controller configured to control the temperature of the medicinal solution contained in the support part; a chamber in which the support part and the controller are installed and an internal temperature of which is adjustable; and a dryer configured to dry the microneedle, wherein the temperature of at least one of the medicinal solution, an internal space of the chamber, in which the microneedle is coated with the medicinal solution, and a space, in which the microneedle is dried, is lowered and is maintained at a predetermined temperature.

In accordance with still another aspect of the present disclosure, there is provided a method of manufacturing a microneedle, the method including adjusting the temperature of a medicinal solution; and coating a surface of the microneedle with the medicinal solution by supporting the microneedle with the medicinal solution, wherein, in the adjusting, the medicinal solution is cooled and is maintained at a predetermined temperature.

According to an aspect of the present disclosure, in the adjusting, the medicinal solution immersed in a support part may be cooled using a cooling member, and then the temperature of the medicinal solution may be maintained at a predetermined temperature using a temperature holding member including a Peltier effect device.

According to an aspect of the present disclosure, the coating may be performed inside a chamber that is cooled to and maintained at a predetermined temperature.

According to an aspect of the present disclosure, the method may further includes drying the microneedle coated with the medicinal solution after the coating, wherein the drying is performed inside a dryer that is cooled to and maintained at a predetermined temperature.

According to an aspect of the present disclosure, the medicinal solution may be prepared by mixing a solvent with a biocompatible substance.

According to an aspect of the present disclosure, the biocompatible substance may include one or more selected from the group consisting of hyaluronic acid, alginic acid, pectin, carrageenan, chondroitin(sulfate), dextran(sulfate), chitosan, polylysine, collagen, gelatin, carboxymethyl chitin, fibrin, agarose, pullulan polylactide, polyglycolide (PGA), a polylactide-glycolide copolymer (PLGA), hyaluronic acid, alginic acid, carrageenan, chondroitin(sulfate), dextran(sulfate), chitosan, polylysine, collagen, gelatin, carboxymethyl chitin, fibrin, agarose, pullulan polyanhydride, polyorthoester, polyetherester, polycaprolactone, polyesteramide, poly(butyric acid), poly(valeric acid), polyurethane, polyacrylate, an ethylene-vinyl acetate polymer, acryl-substituted cellulose acetate, non-degradable polyurethane, polystyrene, polyvinyl chloride, polyvinyl fluoride, poly(vinylimidazole), chlorosulfonate polyolefin, polyethylene oxide, polyvinylpyrrolidone (PVP), polyethylene glycol (PEG), polymethacrylate, hydroxypropyl methylcellulose (HPMC), ethyl cellulose (EC), hydroxypropyl cellulose (HPC), carboxymethyl cellulose, cyclodextrin, and a copolymer of monomers and cellulose forming such a polymer.

According to an aspect of the present disclosure, the medicinal solution may be mixed with an additive for improving mechanical strength, wherein the additive is formed of one or more selected from the group consisting of trehalose, glucose, maltose, lactose, lactulose, fructose, turanose, melitose, melezitose, dextran, sorbitol, xylitol, palatinit, mannitol, poly((lactide), poly(glycolide), poly((lactide-co-glycolide), polyanhydride, polyorthoester, polyetherester, polycaprolactone, polyesteramide, poly(butyric acid), poly(valeric acid), polyurethane, polyacrylate, an ethylene-vinyl acetate polymer, acryl-substituted cellulose acetate, non-degradable polyurethane, polystyrene, polyvinyl chloride, polyvinyl fluoride, poly(vinylimidazole), chlorosulphonate polyolefin, polyethylene oxide, polyvinylpyrrolidone (PVP), polyethylene glycol (PEG), polymethacrylate, hydroxypropyl methylcellulose (HPMC), ethyl cellulose (EC), hydroxypropyl cellulose (HPC), carboxymethyl cellulose, and cyclodextrin and a copolymer of monomers forming such a polymer.

According to an aspect of the present disclosure, the medicinal solution may be mixed with an active ingredient, wherein the active ingredient includes at least any one of a synthetic medicine, a protein/peptide medicine, a hormone, a hormone analogue, an enzyme, an enzyme inhibitor, a signal transduction protein or a portion thereof, an antibody or a portion thereof, a single-chain antibody, a binding protein or a binding domain thereof, an antigen, an adherent protein, a structural protein, a regulatory protein, a toxin protein, a cytokine, a transcription regulator, a blood coagulation factor, and a vaccine.

According to an aspect of the present disclosure, the protein/peptide medicine may include at least any one of vaccines, allergic antigens, insulin, insulin-like growth factor 1 (IGF-1), growth hormone, erythropoietin, granulocyte-colony stimulating factors (G-CSFs), granulocyte/macrophage-colony stimulating factors (GM-CSFs), interferon alpha, interferon beta, interferon gamma, interleukin-1 alpha and beta, interleukin-3, interleukin-4, interleukin-6, interleukin-2, epidermal growth factors (EGFs), calcitonin, adrenocorticotropic hormone (ACTH), tumor necrosis factor (TNF), atobisban, buserelin, cetrorelix, deslorelin, desmopressin, dynorphin A (1-13), elcatonin, eleidosin, eptifibatide, growth hormone releasing hormone-II (GHRH-II), gonadorelin, goserelin, histrelin, leuprorelin, lypressin, octreotide, oxytocin, pitressin, secretin, sincalide, terlipressin, thymopentin, thymosine, triptorelin, bivalirudin, carbetocin, cyclosporine, exedine, lanreotide), luteinizing hormone-releasing hormone (LHRH), nafarelin, parathyroid hormone, pramlintide, enfuvirtide (T-20), thymalfasin, and ziconotide.

According to an aspect of the present disclosure, a solvent may be added to the medicinal solution, wherein the solvent includes at least one of inorganic or organic solvents including distilled water (DI water), methanol, ethanol, chloroform dibutyl phthalate, dimethyl phthalate, ethyl lactate, glycerin, isopropyl alcohol, lactic acid, and propylene glycol.

A microneedle according to a preferred embodiment of the present disclosure is manufactured by a method including a step of adjusting the temperature of a medicinal solution and a step of supporting the microneedle with a medicinal solution to coat a surface of the microneedle with the medicinal solution, wherein, in the step of adjusting the temperature, the medicinal solution is cooled and is maintained at the cooling temperature.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF THE DISCLOSURE

A preferred embodiment of the present disclosure will now be described more fully with reference to the accompanying drawings.

Figure 1:
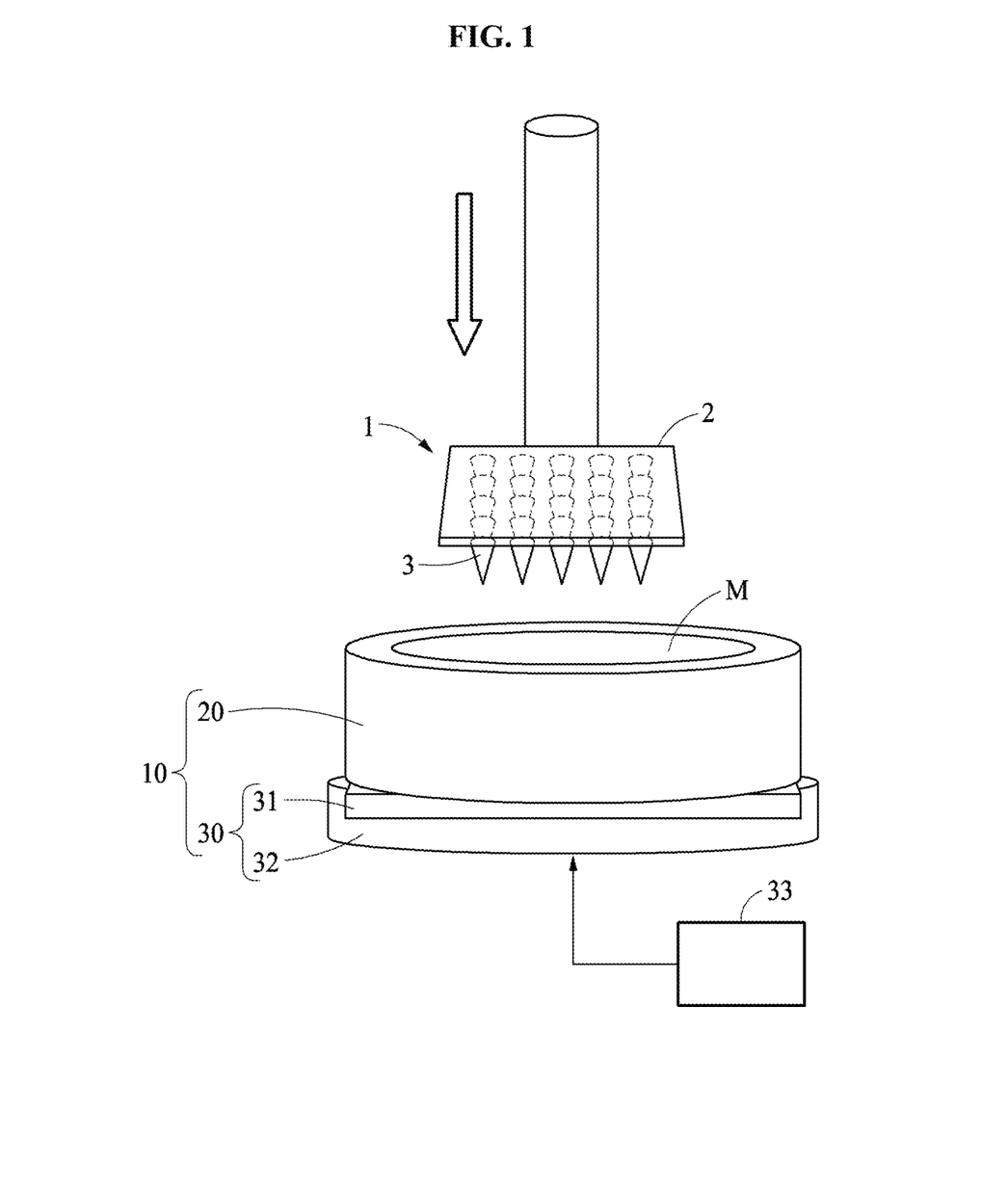
FIG. 1 is a perspective view schematically illustrating an apparatus for manufacturing a microneedle according to a preferred embodiment of the present disclosure.

Referring to FIG. 1, an apparatus 10 for manufacturing a microneedle according to a preferred embodiment of the present disclosure includes a support part 20 and a controller 30.

For reference, the apparatus 10 for manufacturing a microneedle according to a preferred embodiment of the present disclosure is used to manufacture a microneedle 1 coated with a medicinal solution M that penetrates into the skin.

The medicinal solution M for coating the microneedle 1 is contained in the support part 20. The support part 20, which is a container with an open top, contains the medicinal solution M. For reference, although the support part 20 is exemplified as having an open top in FIG. 1, the present disclosure is not limited thereto. That is, the support part 20 may be modified such that a top thereof is selectively covered and opened with a cover.

The controller 30 serves to control the temperature of the medicinal solution M contained in the support part 20. The controller 30 includes a cooling means for cooling the temperature of the medicinal solution M, thereby being capable of controlling the temperature of the medicinal solution M. To accomplish this, the controller 30 includes a temperature holding member 31 and a cooling member 32.

The temperature holding member 31 is installed at the bottom of the support part 20 and serves to maintain the temperature of the medicinal solution M. In this embodiment, the temperature holding member 31 is exemplified as including a Peltier effect device. That is, the temperature holding member 31 may include an electronic cooling element, a Peltier effect device, thereby cooling and maintaining the temperature of the support part 20 using the Peltier effect of heating one side and cooling another side through heat absorption.

The cooling member 32 is provided at the bottom of the support part 20, and the temperature holding member 31 is provided between the cooling member 32 and the support part 20. Accordingly, the cooling member 32 cools heat generated during cooling of the temperature holding member 31 including a Peltier effect device for cooling the support part 20. The cooling member 32 includes a cooling fan connected to a refrigerant source 33 and serves to cool the medicinal solution M contained in the support part 20.

For reference, although the refrigerant source 33 of the cooling member 32 is not illustrated in detail, the refrigerant source 33 may include a refrigerant storage used as a space for storing a refrigerant; a refrigerant inlet that is connected to the refrigerant storage and is used to inject a refrigerant from the outside into the refrigerant storage; a refrigerant outlet that is connected to the refrigerant storage and is used to discharge a refrigerant from the refrigerant storage to the outside; and a cover that is coupled with the refrigerant inlet and the refrigerant outlet and is configured to prevent outflow of a refrigerant.

The controller 30 having the configuration may lower the temperature of the medicinal solution M contained in the support part 20 to a desired temperature, e.g., 4° C. to 15° C., to maintain viscosity suitable for coating. That is, by lowering the temperature of the medicinal solution M, a viscosity range allowing uniform coating of a surface of the microneedle 1 by the medicinal solution M even using a small amount of thickener may be provided.

Figure 2:
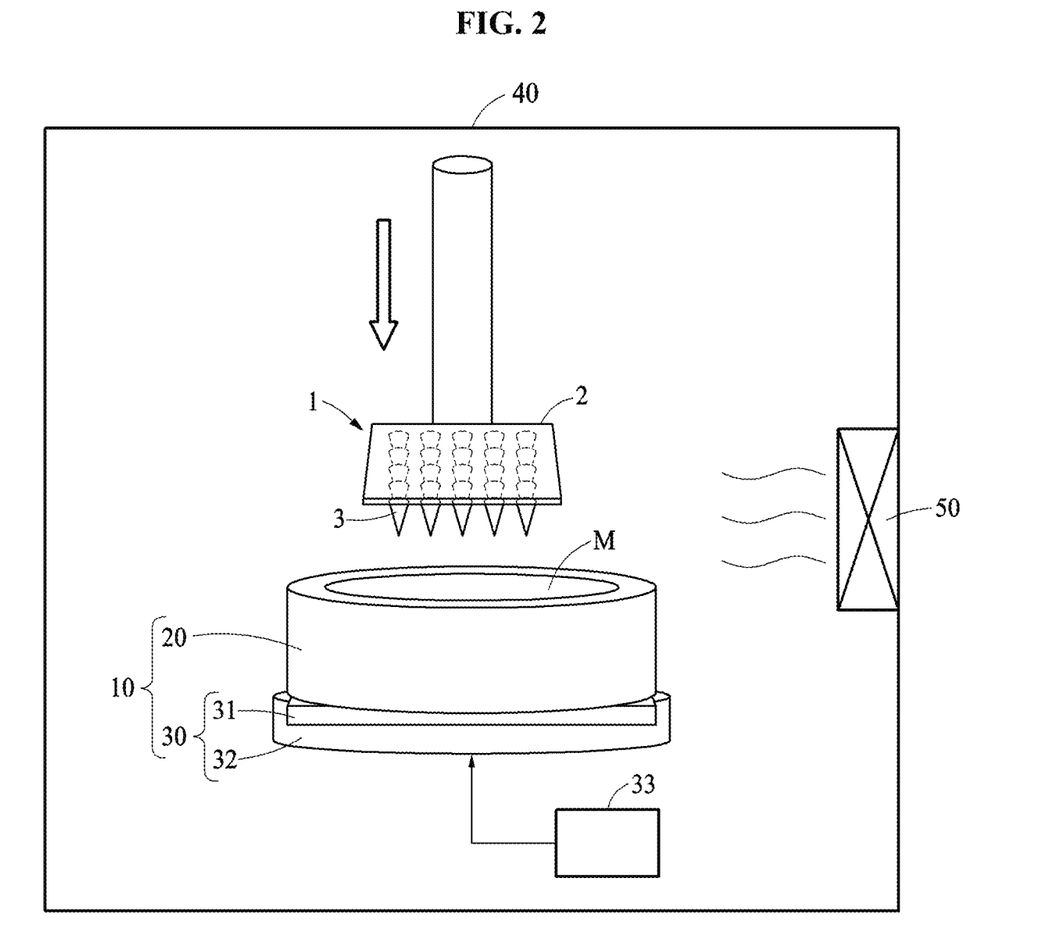
FIG. 2 illustrates another embodiment of the apparatus shown in FIG. 1.

Meanwhile, as illustrated in FIG. 2, the apparatus 10 for manufacturing a microneedle may further include a chamber 40 and a dryer 50.

The chamber 40 may be formed in a closed structure, and the support part 20 and the controller 30 may be installed in the chamber 40. Accordingly, it is possible to prevent foreign matter such as dust from contaminating the microneedle 1 during manufacture thereof and to prevent the temperature around the support part 20, lowered by the cooling member 32, from easily rising. The temperature inside the chamber 40 may be controlled. More particularly, the temperature inside the chamber 40 may be lowered and maintained at a predetermined temperature by a heat exchanger, maintained at a low temperature by a refrigerant, and by forcibly circulating internal air. Accordingly, a process of immersing the microneedle 1 in the support part 20 to coat a surface of the microneedle 1 with a medicinal solution may be performed inside the chamber 40 cooled to a low temperature.

Figure 3:
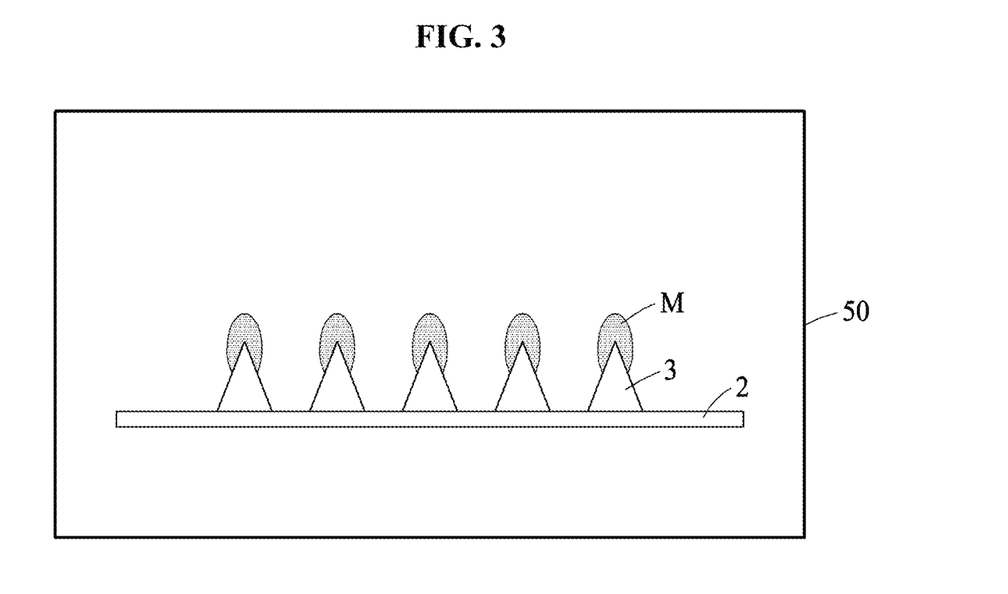
FIG. 3 illustrates another embodiment of a dryer shown in FIG. 1.

The dryer 50 serves to dry a surface of the microneedle 1 that has been immersed in the support part 20 to be coated with the medicinal solution M. In particular, the dryer 50 may be provided as a blower, which is capable of supplying air to the microneedle 1 to dry the microneedle 1, inside the chamber 40 as shown in FIG. 2, or may be formed to include a space capable of containing coated a microneedle 1 as shown in FIG. 3. For example, when the dryer 50 is formed to include a space therein, an internal temperature of the dryer 50 may be adjusted, cooled, and maintained at a predetermined temperature.

Accordingly, the microneedle 1 coated with the medicinal solution M may be dried in a low-temperature environment cooled to a predetermined temperature by the dryer 50.

As described above, a concept including the cooling member 32, the controller 30 including the temperature holding member 31, and the support part 20 may be referred to as a coating device. Such a coating device may be provided in the chamber 40 that is capable of maintaining the coating device at low temperature. In this state, a coating process may be carried out. A drying process may also be carried out in the chamber 40 or dryer 50 that is maintained at low temperature.

In other words, the controller 30 may lower the temperature of the medicinal solution M, with which the microneedle 1 is supported and may maintain the medicinal solution M at a predetermined temperature, the chamber 40 may lower the temperature of an environment or space, in which the microneedle 1 is coated, and may maintain the environment or the space at a predetermined temperature, and the dryer 50 may lower the temperature of an environment or space, in which the microneedle 1 is dried, and may maintain the environment or the space at a predetermined temperature.

Accordingly, viscosity may be controlled and the stability of active ingredients in the medicinal solution may be increased by adjusting the temperature of the manufacturing environment including all of a step of preparing the medicinal solution for coating the microneedle 1, a step of coating the microneedle 1 with the medicinal solution, and a step of drying the medicinal solution according to the present disclosure.

In addition, by lowering the temperature of the medicinal solution M according to the present disclosure, denaturation of the medicinal solution M sensitive to temperature may be inhibited, whereby stability may be increased. In addition, evaporation of a solvent may be inhibited, whereby the microneedle 1 may be uniformly coated with the medicinal solution M without change in the composition of the medicinal solution M during coating.

Figure 4:
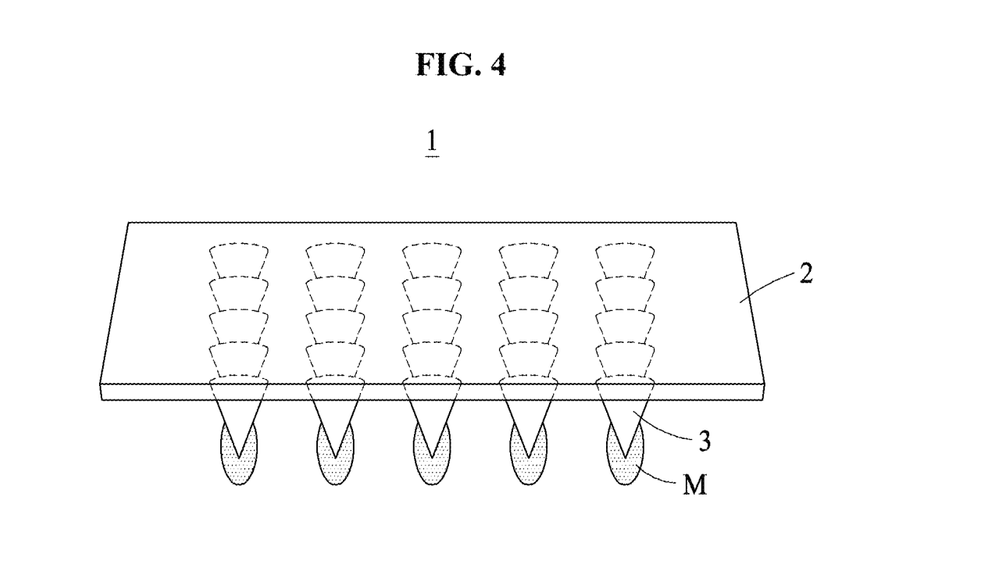
FIG. 4 is a perspective view schematically illustrating a microneedle manufactured using the apparatus shown in FIG. 1.

Referring to FIG. 4, a microneedle 1 manufactured using the apparatus 10 shown in FIG. 1 is illustrated. As shown in FIG. 4, the microneedle 1 is formed of a base 2 and a plurality of tips 3 provided on the base 2. The tips 3 are coated with the medicinal solution M.

More particularly, the tips 3 may be coated with a medicinal solution M that penetrates the skin and is melted therein. The tips 3 have sharp ends for easy penetration into the skin S. Although the tips 3 are illustrated as having a generally conical shape in this embodiment, the present disclosure is not limited thereto. In addition, the number of the tips 3 is not limited to the number of the illustrated tips 3.

The base 2 supports the tips 3. That is, the base 2 is a body of the microneedle 1 and supports all of the tips 3.

Meanwhile, the microneedle 1 is immersed for a predetermined time in the medicinal solution M contained in the support part 20, and then is elevated, as illustrated in FIG. 1, thereby manufacturing the microneedle 1 coated with the medicinal solution M as shown in FIG. 4. The method of manufacturing the microneedle 1 is summarized in FIG. 5.

Figure 5:
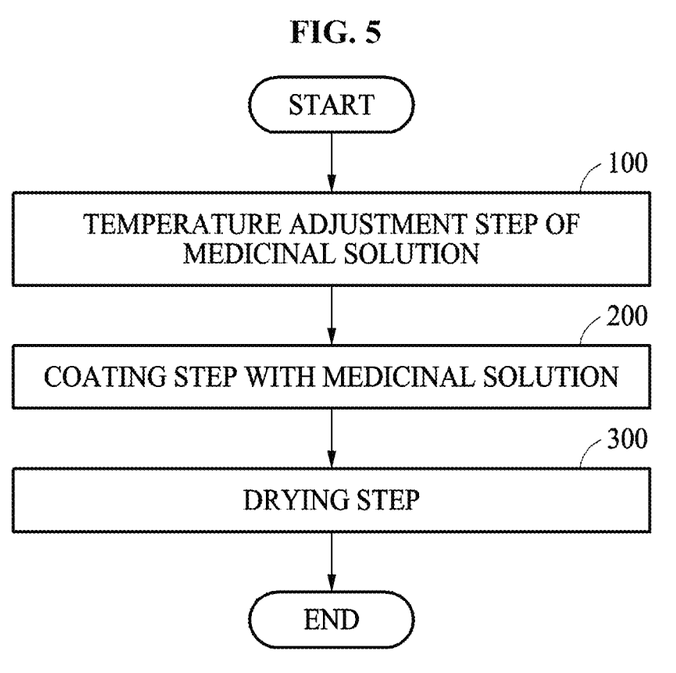
FIG. 5 is a flowchart schematically illustrating a method of manufacturing a microneedle using the apparatus shown in FIG. 1.

As shown in FIG. 5, the method of manufacturing the microneedle 1 includes a step 100 of adjusting the temperature of the medicinal solution M and a step 200 of coating with the medicinal solution M.

In the step 100 of adjusting the temperature of the medicinal solution M, the temperature of the medicinal solution M contained in the support part 20 is lowered to and maintained at a desired temperature by the controller 30. By adjusting the temperature of the medicinal solution M, the viscosity of the medicinal solution M may be maintained at a viscosity suitable for coating.

In particular, in the step 100 of adjusting the temperature of the medicinal solution M, the medicinal solution M contained in the support part 20 is cooled by the cooling member 32, and then the temperature of the medicinal solution M may be maintained at a predetermined temperature by the temperature holding member 31 including a Peltier effect device.

In the step 200 of coating with the medicinal solution M, the microneedle 1 is supported with the medicinal solution M, whereby a surface of the microneedle 1 is coated with the medicinal solution M. That is, the tips 3 of the microneedle 1 are coated with the medicinal solution M by immersing the microneedle 1 in the medicinal solution M, the temperature of which has been adjusted. The step 200 of coating with the medicinal solution M may be performed inside the chamber 40 containing the support part 20, the cooling member 32, and the temperature holding member 31. The interior of the chamber 40, in which the coating step 200 is performed, may be cooled to a predetermined temperature by a heat exchanger and forced convection, and thus, may be maintained at a predetermined low temperature.

The microneedle 1 coated with the medicinal solution M is removed from the support part 20 and is subjected to a drying step 300, thereby producing a final product. The drying step 300 may be performed in the dryer 50 which has been cooled to a predetermined temperature and maintained at the predetermined low temperature, or in the chamber 40 in which the coating process has been performed.

For reference, the medicinal solution M described in the present disclosure is a solution prepared by mixing a solvent with a biocompatible substance. In this embodiment, the medicinal solution M is exemplified as a 1% aqueous polymer solution prepared by dissolving a biocompatible substance including 0.01 g of hyaluronic acid in a solvent including 1 ml of distilled water (DW).

Here, the biocompatible substance includes one or more selected from the group consisting of hyaluronic acid, alginic acid, pectin, carrageenan, chondroitin sulfate), dextran (sulfate), chitosan, polylysine, collagen, gelatin, carboxymethyl chitin, fibrin, agarose, pullulan polylactide, polyglycolide (PGA), a polylactide-glycolide copolymer (PLGA), hyaluronic acid, alginic acid, carrageenan, chondroitin(sulfate), dextran(sulfate), chitosan, polylysine, collagen, gelatin, carboxymethyl chitin, fibrin, agarose, pullulan polyanhydride, polyorthoester, polyetherester, polycaprolactone, polyesteramide, poly(butyric acid), poly(valeric acid), polyurethane, polyacrylate, an ethylene-vinyl acetate polymer, acryl-substituted cellulose acetate, non-degradable polyurethane, polystyrene, polyvinyl chloride, polyvinyl fluoride, poly(vinylimidazole), chlorosulfonate polyolefin, polyethylene oxide, polyvinylpyrrolidone (PVP), polyethylene glycol (PEG), polymethacrylate, hydroxypropyl methylcellulose (HPMC), ethyl cellulose (EC), hydroxypropyl cellulose (HPC), carboxymethyl cellulose, cyclodextrin, and a copolymer of monomers and cellulose forming such a polymer.

In addition, the medicinal solution M is prepared by mixing the biocompatible substance with an additive for improving mechanical strength. The additive is formed of one or more selected from the group consisting of trehalose, glucose, maltose, lactose, lactulose, fructose, turanose, melitose, melezitose, dextran, sorbitol, xylitol, palatinit, mannitol, poly((lactide), poly(glycolide), poly((lactide-co-glycolide), polyanhydride, polyorthoester, polyetherester, polycaprolactone, polyesteramide, poly(butyric acid), poly(valeric acid), polyurethane, polyacrylate, an ethylene-vinyl acetate polymer, acryl-substituted cellulose acetate, non-degradable polyurethane, polystyrene, polyvinyl chloride, polyvinyl fluoride, poly(vinylimidazole), chlorosulphonate polyolefin, polyethylene oxide, polyvinylpyrrolidone (PVP), polyethylene glycol (PEG), polymethacrylate, hydroxypropyl methylcellulose (HPMC), ethyl cellulose (EC), hydroxypropyl cellulose (HPC), carboxymethyl cellulose, and cyclodextrin and a copolymer of monomers forming such a polymer.

In addition, the medicinal solution M is prepared by mixing the biocompatible material with an active ingredient. The active ingredient includes a protein/peptide medicine, but the present disclosure is not limited thereto. The active ingredient includes at least any one of a temperature-sensitive synthetic medicine, a hormone, a hormone analogue, an enzyme, an enzyme inhibitor, a signal transduction protein or a portion thereof, an antibody or a portion thereof, a single-chain antibody, a binding protein or a binding domain thereof, an antigen, an adherent protein, a structural protein, a regulatory protein, a toxin protein, a cytokine, a transcription regulator, a blood coagulation factor, and a vaccine. More particularly, the protein/peptide medicine includes any one of temperature-sensitive influenza vaccines and other vaccines, allergenic and antigenic substances, insulin, insulin-like growth factor 1 (IGF-1), growth hormone, erythropoietin, granulocyte-colony stimulating factors (G-CSFs), granulocyte/macrophage-colony stimulating factors (GM-CSFs), interferon alpha, interferon beta, interferon gamma, interleukin-1 alpha and beta, interleukin-3, interleukin-4, interleukin-6, interleukin-2, epidermal growth factors (EGFs), calcitonin, adrenocorticotropic hormone (ACTH), tumor necrosis factor (TNF), atobisban, buserelin, cetrorelix, deslorelin, desmopressin, dynorphin A (1-13), elcatonin, eleidosin, eptifibatide, growth hormone releasing hormone-II (GHRH-II), gonadorelin, goserelin, histrelin, leuprorelin, lypressin, octreotide, oxytocin, pitressin, secretin, sincalide, terlipressin, thymopentin, thymosine, triptorelin, bivalirudin, carbetocin, cyclosporine, exedine, lanreotide), luteinizing hormone-releasing hormone (LHRH), nafarelin, parathyroid hormone, pramlintide, enfuvirtide (T-20), thymalfasin, and ziconotide.

In addition, a solvent of the medicinal solution M may dissolve a biocompatible substance. Such a solvent may include at least one of inorganic or organic solvents including distilled water (DI water), methanol, ethanol, chloroform dibutyl phthalate, dimethyl phthalate, ethyl lactate, glycerin, isopropyl alcohol, lactic acid, and propylene glycol.

In the following example, microneedles 1 were manufactured using three medicinal solution (M) samples at different temperatures as summarized in Table 1 below.

TABLE 1

|          | Composition         | Temperature |
|----------|---------------------|-------------|
| Sample 1 | CMC 7.05% + DW 92.95% | 10° C.    |
| Sample 2 | CMC 7.05% + DW 92.95% | 25° C.    |
| Sample 3 | CMC 8.2% + DW 91.8%   | 25° C.    |

Here, carboxymethylcellulose (CMC, low viscosity, Sigma) is a thickener, and DW is distilled water.

Figure 6:
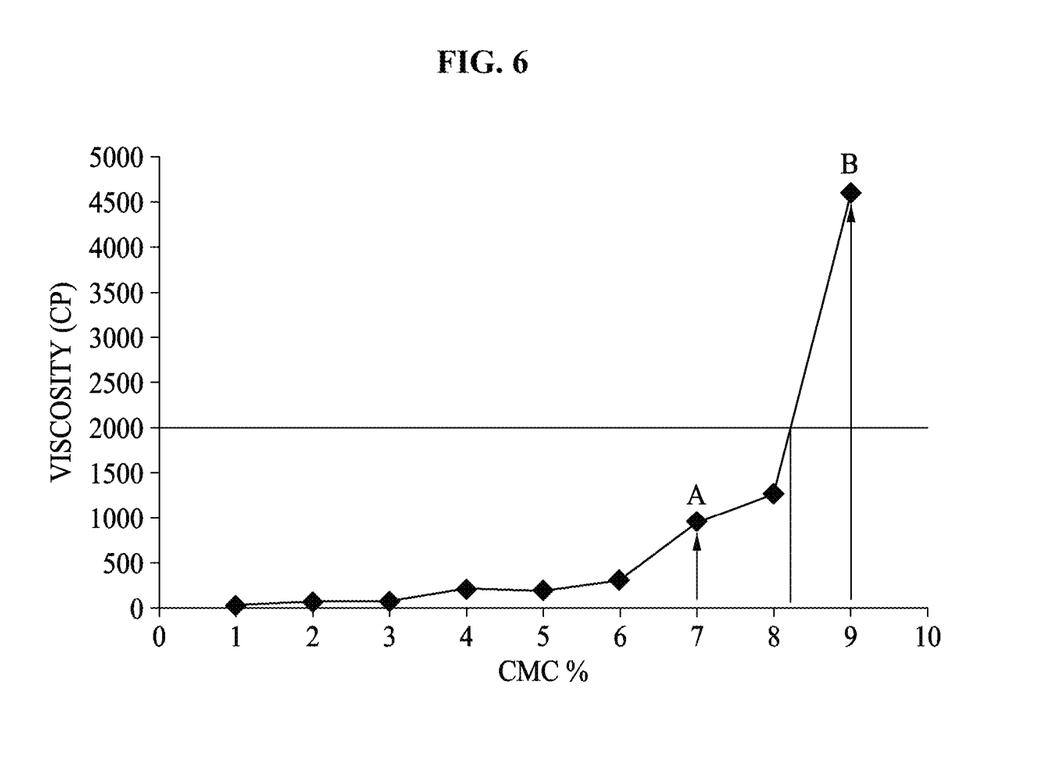
FIG. 6 is a graph schematically illustrating a change in the viscosity of a medicinal solution dependent upon temperature change.

The viscosity of each of the medicinal solution (M) samples having different CMC % among the three samples shown in Table 1 was measured. FIG. 6 illustrates a graph pattern of viscosity change dependent upon thickener type (CMC %-CP). Referring to FIG. 6, temperature-dependent viscosity of each of the three coating solutions having different CMC % summarized in Table 1, i.e., medicinal solutions M, was measured, and a change in the viscosity was observed.

From FIG. 6, it can be confirmed that, when the temperature of Sample 2 is lowered to 10° C., the viscosity is changed from point A, i.e., 936.54 cP, to 1979 cP. In addition, referring to point B of FIG. 6, it can be confirmed that the viscosity of the sample having CMC 9.4% is 4588 cP when the temperature is 25° C., and the viscosity is changed to 9242 cP when the temperature is lowered to 10° C.

Figure 7:
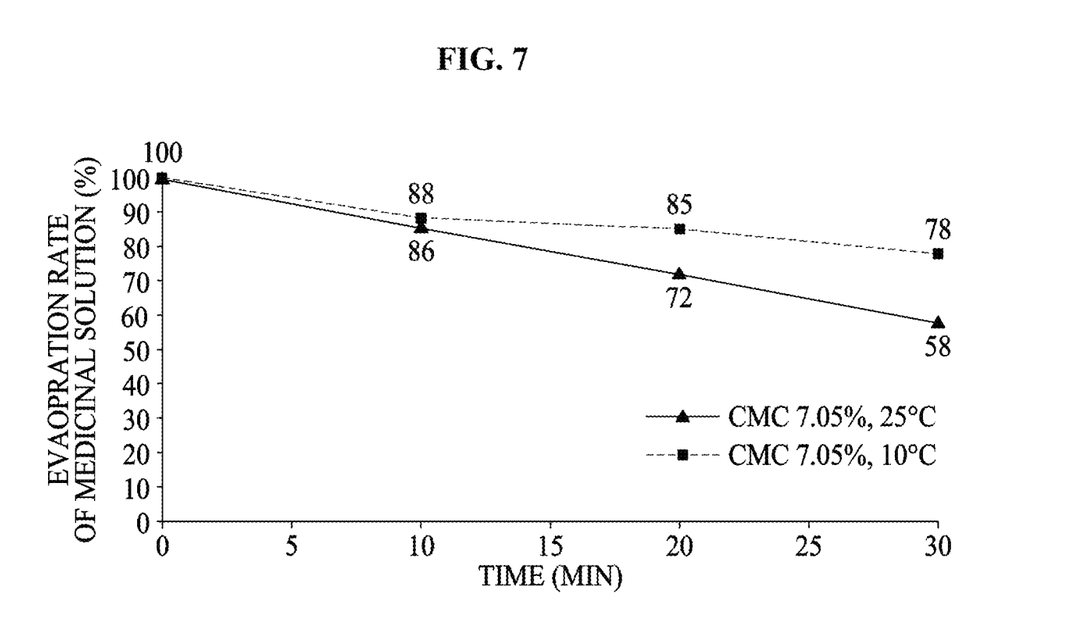
FIG. 7 is a graph schematically illustrating evaporation rates of medicinal solutions using the same thickener, but at different temperatures.

FIG. 7 illustrates a set of graphs of time-dependent evaporation rates of the medicinal solutions M of Samples 1 and 2 shown in Table 1. Referring to the graphs of FIG. 7, it can be confirmed that the time-dependent evaporation rate of the medicinal solution M of Sample 1 is rapidly decreased, compared to that of Sample 2.

Figure 8:
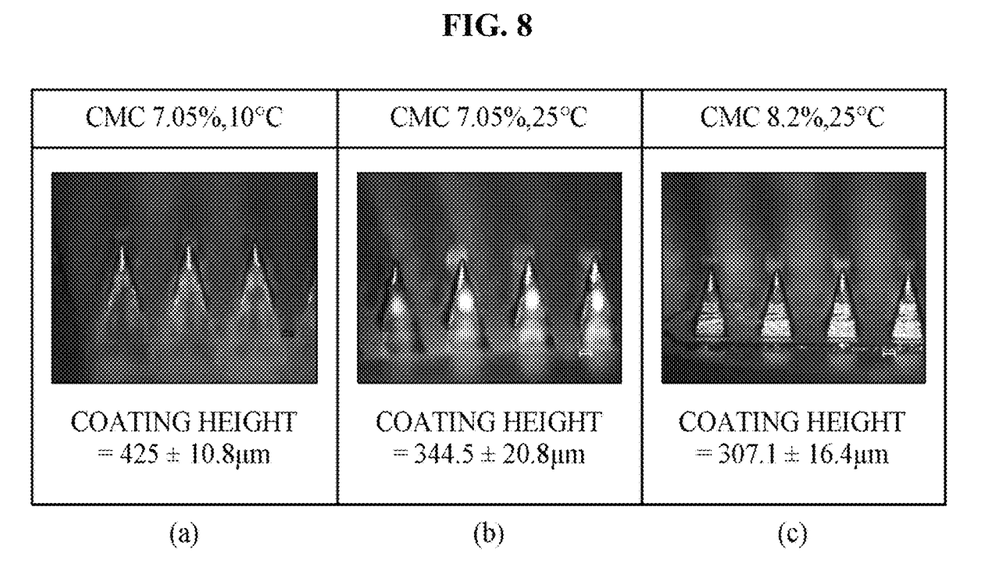
FIG. 8 illustrates surface coating states of a microneedle, respectively coated with three medicinal solutions prepared with different thickeners at different temperatures, photographed by an optical microscope.

FIG. 8 illustrates optical microscopic images to determine whether the microneedles 1 are uniformly coated with the medicinal solutions M of Samples 1 to 3. FIG. 8(a) illustrates the microneedle 1 coated under the condition of Sample 1, wherein a coating height of the microneedle 1 is 425±10.8 μm. In addition, a coating height of the microneedle 1 coated under the condition of Sample 2 is 344.5±20.8 μm as shown in FIG. 8(b), and a coating height of the microneedle 1 coated under the condition of Sample 3 is 307.1±16.4 μm as shown in FIG. 8(c). That is, from FIG. 8, it can be confirmed that a coating height of the microneedle 1 depends upon a coating condition.

Figure 9:
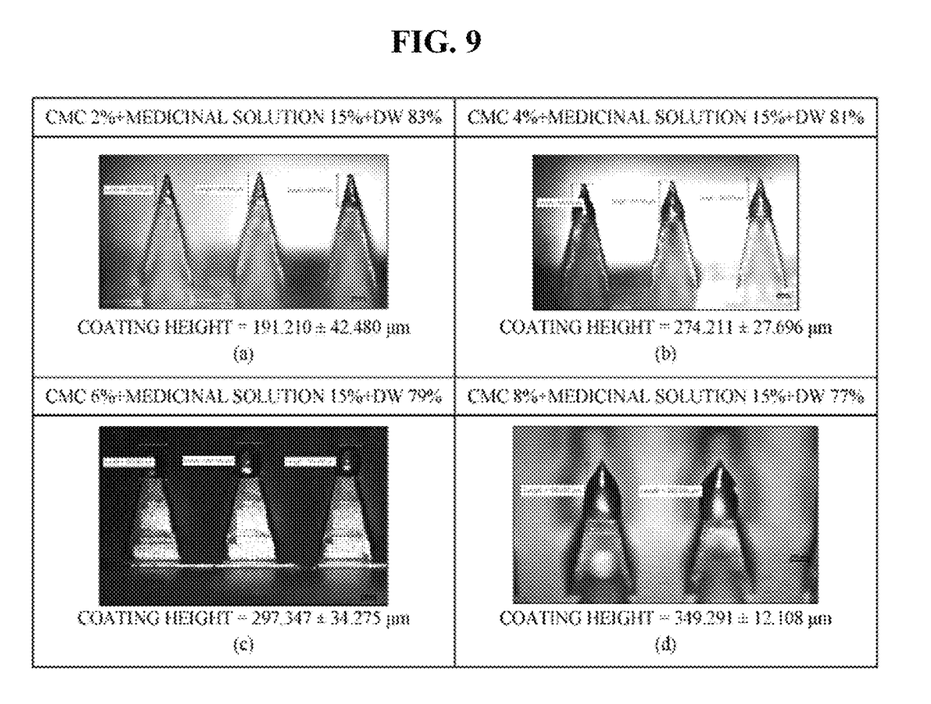
FIG. 9 is a set of optical microscopic images illustrating that surface coating amounts of a microneedle increase with increasing viscosity.

FIG. 9(a) illustrates a result of coating performed under a condition of CMC 2%+medicinal solution 15%+distilled water 83%, FIG. 9(b) illustrates a result of coating performed under a condition of CMC 4%+medicinal solution 15%+distilled water 81%, FIG. 9(c) illustrates a result of coating performed under a condition of CMC 6%+medicinal solution 15%+distilled water 79%, and FIG. 9(d) illustrates a result of coating performed under a condition of CMC 8%+medicinal solution 15%+distilled water 77%. That is, FIG. 9 illustrates optical microscopic images indicating that a surface coating amount of the microneedle 1 tends to increase with increasing viscosity.

A coating height of the microneedle 1 coated with CMC 2%+medicinal solution 15%+distilled water 83% is 191.210±42.480 μm as shown in FIG. 9(a), and a coating height of the microneedle 1 coated with CMC 4%+medicinal solution 15%+distilled water 81% is 274.211±27.696 μm as shown in FIG. 9(b). In addition, a coating height of the microneedle 1 coated with CMC 6%+medicinal solution 15%+distilled water 79% is 297.347±34.275 μm as shown in FIG. 9(c), and a coating height of the microneedle 1 coated with CMC 8%+medicinal solution 15%+distilled water 77% is 349.291±12.108 μm as shown in FIG. 9(d).

As shown in FIG. 9, the microneedle 1 of FIG. 9(d) exhibits the most uniformly coated surface. In this case, a viscosity is about 4500 to 5000 cP, which indicates an excellent coating state.

In accordance the present disclosure with the above configuration, first, a viscosity suitable for coating can be determined by adjusting the temperature of a medicinal solution for coating a microneedle. Accordingly, the medicinal solution can be uniformed spread on a support part, thereby improving coating quality of the microneedle.

Second, by adjusting the temperature of the medicinal solution to a low temperature, denaturation of temperature-sensitive active ingredients in the medicinal solution can be prevented to increase stability, and evaporation of a solvent can be prevented to allow uniform coating without a change in the composition of the medicinal solution during coating.

Third, since viscosity can be easily controlled by adjusting temperature without addition of a large amount of excipient, as a thickener, to a medicinal solution, the content of the medicinal solution coated on the microneedle can be increased.

While the present disclosure has been described referring to the preferred embodiments, those skilled in the art will appreciate that many modifications and changes can be made to the present disclosure without departing from the spirit and essential characteristics of the present disclosure.

DESCRIPTION OF SYMBOLS

1: MICRONEEDLE
2: BASE
3: TIP
10: APPARATUS FOR MANUFACTURING A MICRONEEDLE
20: SUPPORT PART
30: CONTROLLER
31: TEMPERATURE HOLDING MEMBER
32: COOLING MEMBER
40: CHAMBER
50: DRYER
M: MEDICINAL SOLUTION

What is claimed is:
1. An apparatus for manufacturing a microneedle coated with a medicinal solution, the apparatus comprising:

a support part containing a medicinal solution for coating a microneedle; and a controller configured to control the temperature of the medicinal solution contained in the support part, wherein the controller lowers the temperature of the medicinal solution and maintains the temperature at a predetermined temperature, wherein the controller comprises:

a temperature holding member installed at a bottom of the support part and configured to maintain the temperature of the medicinal solution; and a cooling member provided at a bottom of the support part and configured to cool the support part, wherein the temperature holding member is provided between the cooling member and the support part, and wherein the temperature holding member comprises a Peltier effect device, and the cooling member comprises a cooling fan cooled by a refrigerant.

2. The apparatus according to claim 1, wherein the support part is a container with an open top, and the controller is provided at a bottom of the support part and serves to lower the temperature of the support part to a low temperature.

3. The apparatus according to claim 1, further comprising a chamber, wherein the support part and the controller are installed in the chamber and an internal temperature of the chamber is adjustable.

4. The apparatus according to claim 3, wherein an inside of the chamber is cooled and is maintained at a predetermined temperature, and a process of immersing the microneedle in the support part to coat a surface of the microneedle with a medicinal solution is performed inside the chamber cooled to low temperature.

5. The apparatus according to claim 1, further comprising a dryer configured to dry the microneedle coated with the medicinal solution, wherein the dryer serves to adjust temperature.

6. The apparatus according to claim 5, wherein the dryer is cooled and is maintained at a predetermined temperature.

7. An apparatus for manufacturing a microneedle coated with a medicinal solution, wherein the apparatus comprises:

a support part containing a medicinal solution for coating a microneedle;

a controller configured to control the temperature of the medicinal solution contained in the support part;

a chamber in which the support part and the controller are installed and an internal temperature of which is adjustable; and a dryer configured to dry the microneedle, wherein the temperature of at least one of the medicinal solution, an internal space of the chamber, in which the microneedle is coated with the medicinal solution, and a space, in which the microneedle is dried, is lowered and is maintained at a predetermined temperature, wherein the controller comprises:

a temperature holding member installed at a bottom of the support part and configured to maintain the temperature of the medicinal solution; and a cooling member provided at a bottom of the support part and configured to cool the support part, wherein the temperature holding member is provided between the cooling member and the support part, and wherein the temperature holding member comprises a Peltier effect device, and the cooling member comprises a cooling fan cooled by a refrigerant.

* * * * *